United States Patent [19]
Webb

[11] Patent Number: 4,765,730
[45] Date of Patent: Aug. 23, 1988

[54] DOUBLE SCANNING OPTICAL APPARATUS AND METHOD

[75] Inventor: Robert H. Webb, Lincoln, Mass.

[73] Assignee: Eye Research Institute of Retina Foundation, Boston, Mass.

[21] Appl. No.: 777,406

[22] Filed: Sep. 17, 1985

[51] Int. Cl.$^4$ .............................................. A61B 3/10
[52] U.S. Cl. .................................... 351/205; 351/221
[58] Field of Search ....................... 351/205, 211, 221

[56] References Cited

U.S. PATENT DOCUMENTS 4,213,678  7/1980  Pomerantzeff .
4,579,430  4/1986  Bille .................................... 351/206

FOREIGN PATENT DOCUMENTS 85107359.3  6/1984  European Pat. Off. .
84402345.7  11/1984  European Pat. Off. .
  5139959    4/1976  Japan .

OTHER PUBLICATIONS

Retinal Localization of Scotomata by Scanning Laser Ophthalmoscopy, G. T. Timberlake, M. A. Mainster, R. H. Webb, G. W. Hughes & C. L. Tremp, Investigative Ophthalmology & Visual Science, vol. 22, No. pp. 91–97, Jan. 1982.
Flying Spot TV Ophthalmoscope, R. H. Webb, G. W. Hughes, and O. Pomerantzeff, Sep. 1980, vol. 19, No. 17/Applied Optics.
Scanning Laser Ophthalmoscope, Robert H. Webb and George W. Hughes, Jul. 1981, vol. BME-28, No. 7, IEEE Transactions on Biomedical Engineering.
Experimental Observations of the Depth-Discrimination Properties of Scanning Microscopes, D. K. Hamilton, T. Wilson, and C. J. R. Sheppard, Dec. 1981, vol. 6, No. 12/Optics Letters.
Scanning Laser Ophthalmoscopy, Martin A. Mainster, MD, PhD, George T. Timberlake, PhD., Robert H. Webb, PhD, George W. Hughes, ScD, vol. 89, No. 7, Jul. 1982, Ophthalmology.
Holographic Scanner, Glenn T. Sincerbox, Nov./Dec. 1982, Optic News.
Optics for Laser Rasters, Robert H. Webb, Applied Optics, vol. 23, No. 20/15, Oct. 1984.
Improved Imaging with the Scanning Laser Ophthalmoscope, Robert H. Webb, George W. Hughes and Douglas P. Wornson, Winter 1985, Mar. 19–20, 1985, Opt. Assoc. of America Meeting.
Double Scanning and Eye Tracking with a Scanning Laser Ophthalmoscope, Robert H. Webb, George W. Hughes, Douglas P. Wornson, poster paper, ARVO Meeting, Jun. 1985.
Manipulating Laser Light for Ophthalmology, Robert H. Webb, IEEE EMB Dec. 1985, pp. 12–16.

*Primary Examiner*—Rodney B. Bovernick
*Attorney, Agent, or Firm*—Lahive & Cockfield

[57] ABSTRACT

An optical instrument which operates with an incident optical beam scanned at high rates and with correspondingly small sized scanning devices, has a double-scanning optical system. The output reflected beam that is detected overfills the first-stage scanning element, yet the instrument attains a relatively high-contrast image.

30 Claims, 2 Drawing Sheets

DOUBLE SCANNING OPTICAL APPARATUS AND METHOD

The invention was made with the Government support under Grant No. RO1EYO5626 awarded by the National Eye Institute, Bethesda, Md. The Government has certain right in the invention.

FIELD OF THE INVENTION

This invention relates in general to optical instruments and methods, and more particularly to an instrument for scanning a surface or other structure with an optical beam, detecting the light emitted from the structure, and generating a two-dimensional representation of an image of the structure.

BACKGROUND OF THE INVENTION

In the art of optical instruments, it is known to scan a surface to be imaged with a small light source, collect the light reflected from the illuminated spot and direct it to a detector which provides an output signal varying in time in correlation with the scanning of the illuminated spot across the surface. The detector output can be stored in a permanent storage medium or provided directly to a scanning display device, such as a television raster or a cathode ray tube display. By synchronizing the scanning operation of the illuminating source with the scanning of the display signals, a two dimensional image is produced.

One such instrument is a scanning ophthalmoscope which produces an image of the fundus of the eye. It has been found that the use of a laser light source provides improved imaging in an ophthalmoscope. A laser scanning ophthalmoscope is described in U.S. Pat No. 4,213,678. One problem associated with ophthalmoscopes of the type described in U.S. Pat. No. 4,213,678 is that the light collected, at the time the laser is illuminating a particular area on the retina, includes not only light reflected directly from that area, but also light scattered from other surfaces and materials within the eye. This scattered light can cloud or fog the image, since it represents light contributions from other than the specific illuminated area. In an ideal system, each small illuminated area of the target object being examined produces a corresponding image area in the output display, with a brightness or intensity related only to light reflected directly from that target area. In some situations, on the other hand, the scattered light by itself, to the degree that it can be separated from the light directly reflected from the iluminated target area, is useful for diagnostic purposes.

In a device as decribed in the noted patent, the entrance pupil for the scanning laser beam has a small cross sectional area within the pupil of the eye, typically 0.5 mm in diameter, whereas the exit aperture for the reflected light is the overall pupil of the eye, which typically is nine mm in diameter. The detector is placed in a plane conjugate to this exit aperture. In the embodiment described in the patent, the scanning is effected by deflection galvanometers. The horizontal galvanometer is driven at 15.75 kHz. in order to match the horizontal scan frequency of a conventional television sweep, which preferably is used to display the output image. The vertical galvanometer is driven at 60 Hz to produce 525 lines per frame of the output image, again corresponding to the generation of a conventional television raster.

In a scanning ophthalmoscope of this type, the resolution in the raster display of the retinal image directly corresponds to the cross sectional area of the laser spot as it scans the retina. The contrast of the ultimate image depends, at least in part, upon the proportion of light received by the detector which is directly reflected from the illuminated area. Thus, to the extent that scattered light indirectly reaches the detector at the same time as it receives the light directly reflected from the illuminated area, the image is fogged and the contrast is reduced. The term "reflected" is used herein in a broad sense to refer to all optical energy returned by the target structure, it hence includes returned optical energy that results from both specular and diffuse reflection.

One technique used in some optical instruments to improve contrast for images of this type may be termed double scanning. According to this technique, the optical system is arranged to provide that the light reflected from the illuminated target area is selected with a scanning-like action related to the scanning of the incident illumination in such a manner that, at a given instant, the reflected light received by the detector is only that which is reflected from the illuminated target area. In effect, as applied to an ophthalmoscope, the fundus conjugate plane thereby allowing discrimination, at the conjugate retinal plane, between the light directly reflected from the retinal locus and that scattered either anteriorly or positiorly, i.e. within the retina. This approach, however, has been deemed to be unsuitable for an instrument like the laser ophthalmoscope of the type described, because in that instrument the exit aperture for the reflected light is so large that the returning reflected beam was deemed to require an unduly large scanning element. Since, at the driving frequencies associated with a television raster, a deflection galvanometer is limited by mass considerations to a very small surface, in the order of three millimeters, a reflection galvanometer large enough to encompass the returning image has been deemed not feasible.

Another deflection element which has been used for scanning optical instruments is a multifaceted rotating polygon, which would have to rotate at sufficiently high speeds to produce a horizontal scan matching the television frequencies. However, once again the size of the facet required to encompass the image received from the eye's exit aperture is prohibitively large in terms of fabricating a polygonal reflector to rotate at the required speeds.

The acousto-optical deflector is also not available in a form considered suitable for the reflected beam in such an instrument, due to aperture limitations.

OBJECTS OF THE INVENTION

It accordingly is an object of the present invention to provide an optical system for producing a two-dimensional representation of the reflection characteristics of a scanned structure and having relatively high resolution and contrast.

Another object of the invention is to provide an optical instrument having double scanning, i.e. of both incident and reflected light, at high frequencies such as are conventional in a television-type raster display.

It is also an object to provide an ophthalmological instrument for providing a two-dimensional representation of reflection characteristics of structure within an eye essentially in response only to light reflected from the eye structure in a selected manner. In one particular embodiment, the image is created in response essentially to directly reflected light; an in another embodiment in response to indirectly reflected light.

It is another specific object of this invention to provide an ophthalmological instrument for providing a two-dimensional representation of the reflection characteristics of the fundus of an eye wherein the contrast of the ultimate image is enhanced by enabling essentially only directly reflected light to generate that image.

Other objects of the invention will in part be obvious and will in part appear hereinafter.

SUMMARY OF THE INVENTION

It has been found, in one practice, that a double scanning optical instrument can be constructed utilizing a laser source and a multifaceted polygonal reflector for horizontal scan, with a reflection galvonometer or other scanning element for vertical scan, where the facet size in the direction of scan for the polygonal reflector is necessarily small and the reflected beam from the exit aperture of the system is substantially larger than that facet dimension. In the illustrated embodiment described below, the small facets of the polygonal reflector intercept less than 20% of the reflected light from the exit aperture. However, unexpectedly, under these circumstances the instrument attains a significant improvement in contrast over a single scan system, despite the significant loss of throughput.

It has thus been found that an optical instrument, of the type which responds to light energy responsive to a scanned incident beam, can be provided with double scanning with at least one scan element having such a small size that the exit beam overfills it. That is, this scan element is of such small size that it intercepts only a portion of the exit beam. In spite of the resultant loss of exit beam energy, the double-scanning instrument attains images having significant improvements over those of prior instruments. An instrument according to the invention attains this improved performance even when configured to have a large optical exit aperture, as is often desired.

DESCRIPTION OF THE DRAWINGS

For a fuller understanding of the nature and objects of the invention, reference may be made to the following description and the accompanying drawing, in which.

DESCRIPTION OF THE PREFERRED EMBODIMENT

Figure 1:
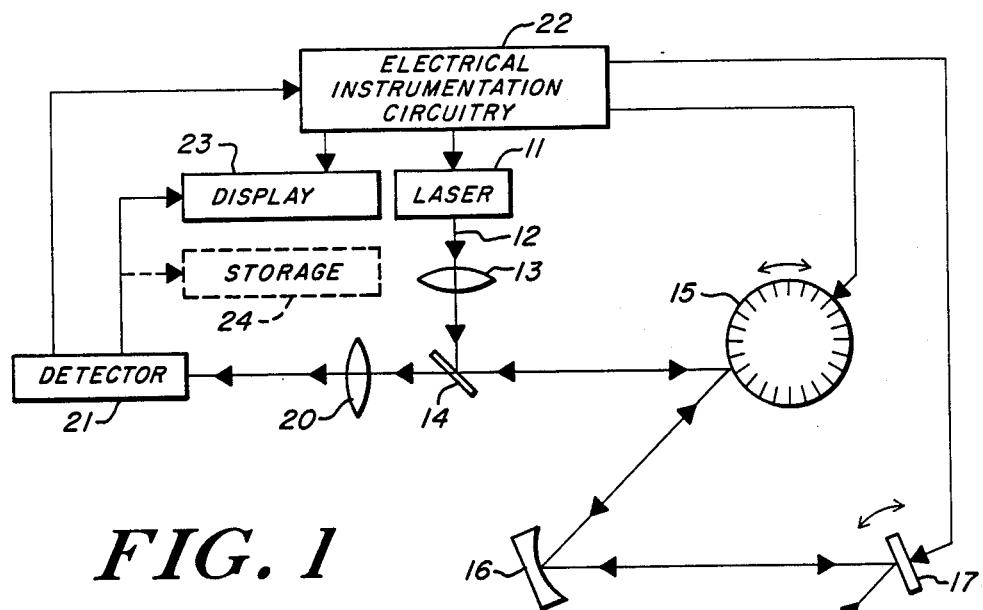
FIG. 1 is a diagrammatic representation of a scanning ophthalmoscope according to the invention.

FIG. 1 shows an embodiment of the invention in the form of an ophthalmoscope 10. A laser illumination source 11 produces a narrow incident light beam 12 which passes through a shaping lens 13 which produces a slightly converging beam that impinges on a small turning mirror 14. The mirror 14 directs the incident laser beam onto facets of a multi-faceted rotating polygonal reflector scanner 15, which provides a horizontal scanning motion of the incident beam. The incident beam is reflected from this first stage scanning element onto a focusing mirror 16, which directs the beam onto the reflecting surface of a galvanometer reflector scanner 17 to produce a vertical scanning motion. From the galvanometer reflector scanner 17, which is a second stage scanning element, the laser input beam is directed onto a second focusing mirror 18, for focusing it onto the fundus 19a of the eye 19 of a subject. The incident beam enters the eye through the pupil.

The reflected light from the fundus 19 is directed back over a common portion of the foregoing optical input path, which includes focusing mirror 18, the second stage scanner 17, focusing mirror 16 and the first stage scanner 15. The reflected output beam from the first stage scanner 15 in large part passes by the turning mirror 14 and hence separates from further traverse along the incident optical path. The output beam instead is directed through a focusing lens 20 and onto an optical detector 21.

The detector 21 is electrically connected to an electrical instrumentation unit 22 which provides electrical control signals to the laser source 11 and electrical drive signals to the scanning deflection elements 15 and 17. In essence, the instrumentation unit provides synchronization of the signals received at the scanning elements 15 and 17 so that the temporal order of the signals produced by the detector 21 can be correlated with the location of the scanned incident laser beam on the surface of the fundus. The control and synchronization which the instrumentation unit provides enables a two-dimensional display device 23, such as a television raster device, to form a two-dimensional display of an image of the eye fundus 19a, in response to the electrical signal which the detector produces in response to the reflected optical energy it receives. The detector signal may be applied to a long term storage element 24, such as a video tape recorder, for subsequent readout and display. For a description of a suitable electrical timing and control circuit, reference is made to U.S. Pat. No. 4,213,678 which is incorporated herein by reference.

THE LASER GENERATOR

The laser 11 can be any suitable laser light source which provides emission at frequencies yielding appropriate contrast for the fundus, or other target. Typically, the laser 11 is an Argon-Krypton laser or Helium-Neon laser operated at a power level to produce an illumination irradiance of one hundred microwatts per square centimeter at the fundus.

THE INPUT OPTICAL SYSTEM

The purpose of the input optical system is to scan the fundus with a narrow optical beam to sequentially illuminate small segmental areas across the fundus surface in a known pattern so that the reflected light detected in time sequence can be electrically converted to a two-dimensional representation of the reflection characteristics of the fundus. In one illustrative instrument, the input optical system forms the incident laser beam with a cross sectional area of substantially 0.5 mm diameter at the entrance pupil of the eye and focussed on the fundus to produce a spot approximately twelve microns in diameter. The horizontal scanning motion in the illustrated preferred embodiment is provided by a multi-faceted polygonal reflector scanner 15 which is rotated by an electric motor at speeds sufficient to produce a scanning frequency of 15.75 kHz to be compatible with a TV sweep frequency. A polygon of (m) facets turns the incident laser beam through a scan angle of 720/m degrees. Thus, if, for example, there are twenty-four facets on the polygon, it must rotate at 40,000 rpm in order to generate the 15.75 kHz scanning frequency. In order to rotate at this speed the moment of inertia of the polygon must be kept small. In one practical embodiment, each facet is six mm wide. The polygonal rotating reflector of the scanner 15 can be obtained commercially from Lincoln Laser (Phoenix, Ariz., No. PO-24 (A grade, G Grade).

The vertical scanning motion in the illustrated preferred embodiment is introduced by a deflection galvanometer 17 that provides a scan action which corresponds with the television vertical scan of 60 Hz. Galvanometer controls, such as those manufactured by General Scanning of Watertown, Mass., are suitable for driving and controlling the position of the galvanometer mirror. The mirror 17 can, for example, be a type G-120D General Scanning mirror.

With this structure and optical alignment in the instrument 10, the illustrated laser beam of 0.5 mm in diameter which it produces underfills each mirror facet of the polygon scanner 15, which, in the same illustrative embodiment, is six mm wide. The beam scanning pivots about a point approximately in the plane of the eye's pupil.

The turning mirror 14 preferably is a stationary mirror reflector. It is small in size in order to produce a minimal shadow in the output beam, and hence preferably is only large enough to intercept the input beam which the focusing element 13 directs, via the turning mirror, to the first stage scanner 15.

Figure 2:
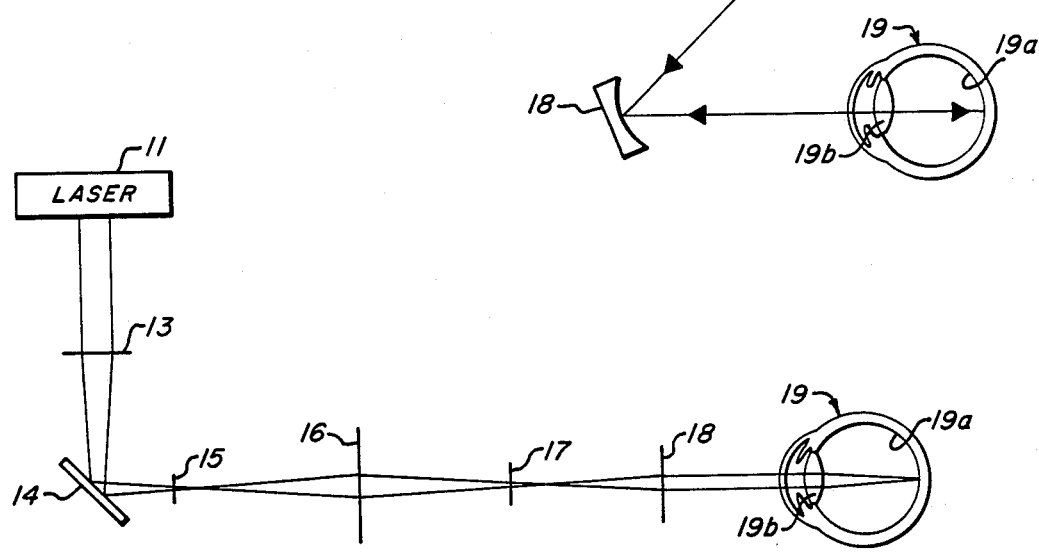
FIGS. 2 and 3 are explanatory ray diagrams of optical beam features of the embodiment illustrated in FIG. 1.
Figure 4:
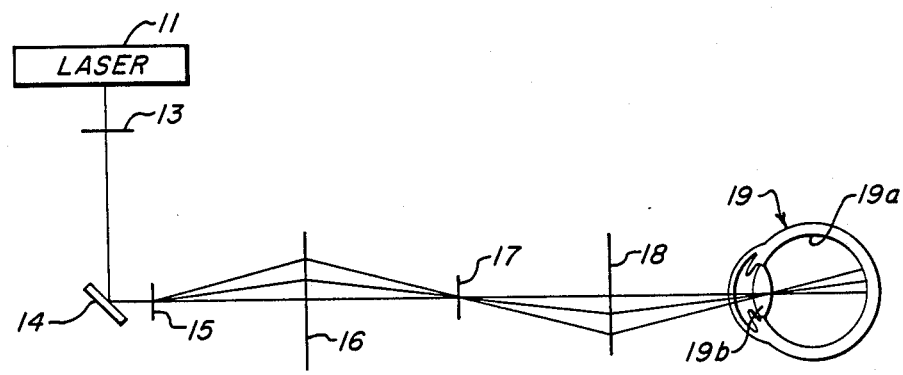

FIGS. 2 and 4 illustrate features of the input optical system. FIG. 2 represents the input beam with the scanners assumed to be stationary in a neutral, non-deflecting, position. The narrow collimated incident beam 12 from the laser is, in this partial representation, shaped by the optical elements 13, 14, 16 and 18, aside from the eye 19 of the subject. The incident beam is in focuse at the retina 19a. The limiting aperture formed by the entrance pupil of the eye 19 is conjugate at the scanners 15 and 17.

FIG. 4, which represents scan features of the input system, illustrates the input beam instantaneously as a single ray which each scanning element moves, as a function of time. The drawing shows, in effect, a time exposure. The illustrated rays intersect at each scanner and at its conjugates, which, for the scanned input beam includes the entrance pupil. The scan angle is the full angle of the envelope of these rays in the plane of the scan.

THE OUTPUT OPTICAL SYSTEM

As noted, a major portion of the output optical system has a common optical path with the input system. This common path includes both of the scanning elements 15 and 17. In the illustrated instrument, it also includes the two focussing elements 16 and 18. However, in the output system, the light reflected from facets 15a of the rotating polygon scanner 15 passes around the turning mirror 14 and is incident on the detector optical system, which includes lens 20 and detector 21.

Figure 3:
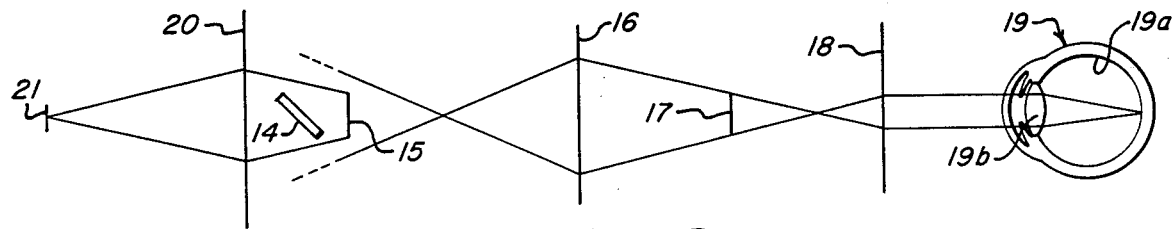

FIG. 3 represents the output beam without regard to the scanning elements 15 and 17, i.e. in the same manner as the representation in FIG. 2. As illustrated, the reflected beam from the fundus preferably has an exit aperture of substantially the entire pupil of the eye, with a diameter of as much as nine mm. The image of this aperture at its conjugate plane also is nine mm., absent magnification. The reflected output beam from the illuminated area on the fundus likewise is approximately nine mm in diameter at any conjugate of the exit pupil, which is where the scan elements 15 and 17 are located.

The ophthalmoscope 10 can have a small entrance pupil, as described above, due to the large radiance of the incident beam. The output beam, however, has relatively low radiance, and hence the provision of this large output pupil is desired to collect a maximal amount of output light energy. The large exit aperture hence enhances the high efficiency of the instrument. It also facilitates viewing a large portion of the eye fundus.

FIG. 3 also illustrates, with exaggerated scale, that the output beam passes around the turning mirror 14, which hence casts a small shadow generally of low significance.

Figure 5:
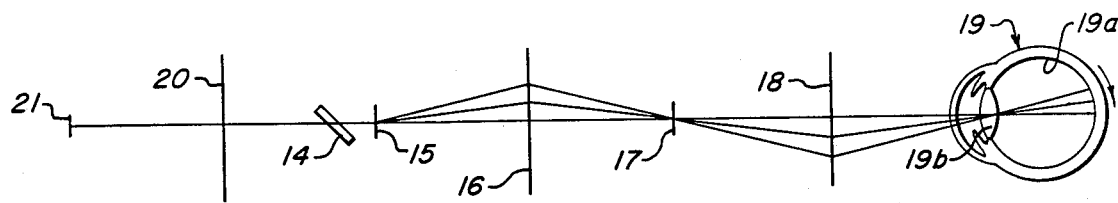
FIGS. 4 and 5 are explanatory ray diagrams of optical scan features of the embodiment of FIG. 1.

FIG. 5 represents scan aspects of the output beam, in the same manner as the scanned input beam representation in FIG. 4. The scanned output rays intersect, and the envelope of the scanned rays has minimal cross-section, at the pupilary plane of the eye 19 and at the scanning elements 15 and 17; this is the same as for the scanned input beam, FIG. 4. The former is at the plane of the exit pupil and the latter are at planes conjugate to it.

As also illustrated in FIG. 3, the relatively large cross-section of the output beam overfills each facet on the polygonal reflector scanner 15. With the six mm facet width of the illustrated embodiment, this overfill corresponds to a loss of throughput of approximately 80%. However, the reflected output light beam which the scanners 15 and 17 direct to the detector 21 is directly reflected substantially exclusively from the illuminated segmental area of the fundus. The detector 21 hence receives a minimal level of scatter or other unwanted light energy. These features enable the instrument to attain a resultant improvement of contrast at the detector which is unexpectedly high, and to yield a substantial improvement in contrast in the resultant image.

The placement in the instrument 10 of the detector 21 at the retinal conjugate plane, as apparent in FIG. 3, is advantageous because it allows the detector to have a small aperture. Optical detectors of this type have numerous advantages over large-aperture detectors. In particular, an avalanche diode detector 21 is highly suitable for use as the detector in this system.

If the polygonal reflector 15 is formed with twenty-five facets, distortions due to facet-to-facet and other variations remain stationary in the displayed raster image, since it is evenly divisable into 525 television lines. For this reason, it is deemed preferable that the polygonal sacnner have a number of reflective facets equal to an integral multiple of twenty-five. Further, as described above, there is a common optical path from the horizontal scanner 15 to the target object (in this example, the fundus of the eye) for the scanning beam and for the reflected light. Under these circumstances any reflection of the input laser beam from elements in the common optical path will appear as a noise signal to the detector. The focusing elements 16 and 18 accordingly in most instances are front-surface mirrors, rather than lenses.

While the instrument 10 has been described in terms of the advantages of de-scanning to produce signals corresponding only to light reflected directly from the illuminated target area, there are situations in which it is advantageous to look only at indirectly reflected light. This can be accomplished by moving the detector off the optical axis of the system so that it is in effect looking at target areas displaced from the direct illumination of the input beam. It has been found that information provided from these reflections also is useful in determining characteristics of an eye fundus. An alternative arrangement for attaining this response to only indirect illumination is to image on the detector a target area concentric with, and larger than, the illuminated area, and to mask light reflected from the illuminated area, e.g. with a dark-field or central stop.

Moreover, if the detector is moved axially, the plane of the image can be moved to positions anterior to the retinal surface and thus various types of floaters, such as vitreous spots and strands may become visible in the image. Similarly, movement of the image plane to posterior, sub-surface positions enables the instrument to image interior structure of the eye fundus.

The 15.75 kHz horizontal scan frequency and the 60 Hz vertical scan frequency described above for the illustrated embodiment are for use with television standards adopted for the USA. These values can be selected to suit other standards in practice in other countries. For example, the standard which operates with 625 lines per frame, requires the same 15.75 kHz horizontal scan frequency and a 50.4 Hz vertical scan frequency.

While the invention has been described in terms of an ophthalmoscope embodiment, the same principles can apply to the imaging of reflection characteristics of planes and structures other than the fundus of an eye with enhancement of the contrast characteristics of the representation. Note that the optical system of an instrument according to the invention does not focus the image of the object being scanned to produce an output image, but rather converts a selected portion of the reflected light to a time varying electrical signal, which can then used to drive a synchronized imaging device and reproduce a representative visible image of the area being scanned.

Other embodiments of the invention including modifications of and deletions from this disclosed embodiment will accordingly be apparent to those skilled in the art and are within the scope of the following claims.

What is claimed as new and secured by Letters Patent is:

1. Scanning ophthalmoscope apparatus for providing a two-dimensional output representation of the optical reflection characteristics of a scanned eye fundus, said apparatus comprising
   an optical source for generating an optical input beam of defined cross sectional area,
   a first scanning element comprising a rotatable multifaceted polygonal reflector positioned to intercept said input beam and to reflect said input beam onto the eye fundus to be scanned,
   means for rotating said polygonal reflector at a sufficient speed to generate a scanning motion of said input beam along a first coordinate on said fundus at a predetermined frequency, the dimension along said first coordinate of each facet of said polygonal reflector being large compared to the cross sectional area of said input beam in the scanning direction,
   means for directing light reflected from said scanned fundus back onto the same facet of said polygonal reflector which reflected the light from the input beam onto the object, said reflected light being collected across a cross sectional area which is large compared to the dimension in the scanning direction of said reflecting facets,
   optical detector means positioned to receive the light collected from said scanned fundus, which is reflected back from said polygonal facet, to provide a time varying output signal correlated with the scanning frequency of said input beam, and
   output means for receiving said time varying signal.

2. Apparatus according to claim 1 in which said output means includes display means for displaying an image in response to said time varying signal and having variations in said image corresponding with variations in light directly reflected from the scanned fundus.

3. Apparatus in accordance with claim 2 wherein the rotational speed of said polygonal reflector is such that the scanning frequency of said input beam is substantially 15.75 kHz and wherein said output means includes a television-type raster imaging device.

4. Apparatus in accordance with claim 2 wherein said output means includes a multiple line raster imaging device and wherein said rotating polygonal reflector has a number of facets which is evenly divisible into the number of displayed raster lines.

5. Apparatus in accordance with claim 3 further comprising a second scanning element positioned in the optical path of said input beam from said source and first scanning element for directing said input beam onto the fundus to be scanned and for moving said input beam in a direction normal to the direction of said first coordinate, said second scanning element being operated to produce a scanning frequency in the direction normal to said first coordinate direction of substantially 60 Hz.

6. Apparatus in accordance with claim 5 wherein said rotating polygonal reflector has a number of facets which is evenly dividable into the number of displayed raster lines.

7. Apparatus in accordance with claim 1 further including a second scanning element positioned in the optical path of said input beam from said source and first scanning element for directing said input beam onto the fundus to be scanned and for moving said input beam in a direction normal to the direction of said first coordinate.

8. Apparatus in accordance with claim 3 wherein said second scanning element includes a reflecting galvanometer.

9. Apparatus in accordance with claim 1 wherein the cross-sectional area of said collected light is defined by the image at a conjugate plane of an optical exit aperture which is substantially larger than the cross sectional area of said input beam.

10. Apparatus in accordance with claim 1 wherein said detector is positioned to receive substantially only light reflected directly from the specific portion of the scanned fundus which is illuminated by the input beam at any given time.

11. Apparatus in accordance with claim 1 wherein said detector is positioned to receive only light reflected from a specific portion of said scanned area which is illuminated indirectly from the portion of said scanned area which is illuminated directly by the input beam at any given time.

12. Apparatus in accordance with claim 1 in which said optical source includes a laser for generating said input beam.

13. Apparatus in accordance with claim 1 wherein said optical detector means is an avalanche diode.

14. Scanning ophthalmoscope apparatus for providing a two-dimensional output representation of reflection characteristics of an eye fundus, said apparatus comprising a laser source for generating a laser beam of defined cross sectional area which is small compared to an area of the fundus which is to be scanned, an optical system for directing said laser beam through the pupil of the eye onto said fundus area, said optical system including a first scanning element comprising a multi-faceted rotating polygonal reflector and driving means for rotating said polygonal reflector to scan said laser beam along a first coordinate across an area of said fundus, said optical system including means for collecting light reflected from said scanned area and providing an exit aperture for the reflected light from said area and defined by the pupil of said eye, said optical system directing collected light back along the same optical path by which said laser beam was directed from said polygonal reflector onto said fundus, the cross sectional area of said collected light beam reflected from said fundus as it impinges upon said polygonal reflector being large compared to the dimension of facets of said polygonal reflector along the coordinate of scan, and detector means positioned to receive said reflected light from said polygonal reflector to generate a signal varying in time with the amount of light reflected from said polygonal reflector onto said detector means, and display means for providing said two dimensional output representation of said eye fundus in response to said detector signal.

15. Opthalmoscope apparatus in accordance with claim 14 wherein said optical system further includes a second scanning element arranged in optical alignment between said first scanning element and the eye to be scanned, for moving said scanning laser beam in a direction normal to said first coordinate to effect a two-dimensionl scan of said retinal area.

16. Opthalmoscope apparatus in accordance with claim 15 wherein said polygonal reflector is rotated at a speed to produce a scanning frequency along said first coordinate on said fundus area of substantially 15.75 kHz and said second deflection element produces a scanning motion in a direction normal to said first coordinate at substantially 60 Hertz and wherein said display means includes is a television raster device.

17. A scanning opthalmoscope in accordance with claim 14 wherein said scanning laser beam is directed through a pivot point in a plane having a location selected relative to the laser beam for introducing the scanning laser beam into the eye being examined so located through a small portion only of the eye pupil, and wherein said scanning beam travels from said pivot point onto a wide-angle region of the fundus of the eye located with the eye pupil at said selected plane.

18. Apparatus in accordance with claim 14 wherein the size of the cross sectional area of said reflected beam is defined by the image at a conjugate plane of the exit aperture of said system, the exit aperture of said system being substantially larger than the entrance aperture for said scanning laser beam.

19. A scanning opthalmoscope in accordance with claim 14 wherein said detector is positioned to receive substantially only light reflected directly from the specific portion of the scanned area which is illuminated by the laser beam at any given time.

20. Apparatus in accordance with claim 14 wherein said detector is positioned to receive only light reflected from a specific portion of said scanned area which is illuminated indirectly from the portion of said scanned area which is illuminated directly at any given time.

21. Scanning opthalmoscope apparatus for providing a two-dimensional output representation of the optical reflection characteristics of a scanned fundus, said apparatus comprising an optical source for generating an optical input beam of defined cross sectional area, a first scanning element having reflecting means positioned to intercept said input beam and to reflect said input beam onto the fundus to be scanned, means for operating said first scanning element at a sufficient speed to generate a scanning motion of said input beam along a first coordinate on said object at a predetermined frequency, the dimension along said first coordinate of said reflecting means being sufficiently large compared to the cross sectional area of said input beam in the scanning direction to intercept and reflect substantially all of said input beam, means for directing light reflected from said scanned fundus back onto the same reflecting means of said first scanning element which reflected light from the input beam onto the fundus the dimension along said first coordinate of said reflecting means being sufficiently small relative to the cross-sectional area of said output beam to intercept and reflect only a portion of said output beam, optical detector means positioned to receive the light collected from said scanned fundus, which is reflected back from said first scanning element, to provide a time varying output signal correlated with the scanning frequency of said input beam, and output means for receiving said time varying signal.

22. A method for providing a two-dimensional output representation of the optical reflection characteristic of a scanned fundus, said method comprising the steps of A. directing an optical input beam of selected cross-sectional area onto reflective means of a scanning device, and operating said scanning device to scan light reflected from said reflective means onto a segmental portion of the fundus with a scanning motion of selected rate along a first coordinate, B. configuring said reflective means to intercept and reflect to the fundus substantially all of said input beam, C. directing light reflected from the scanned fundus back to said reflective means of said scanning device, D. forming said reflected light into an output optical beam which overfills said reflective means along said first coordinate, so that said first scanning reflects only a portion of the output beam at any time, E. detecting the portion of the output optical beam reflected by the first scanning device to provide a time-varying electrical signal correlated to the scanning rate of said input beam, and F. producing said output representation in response to said time varying signal.

23. A method according to claim 22 comprising the further steps of

A. illuminating said fundus with said scanning input beam through a selected small input aperture, B. illuminating said detector with said output beam through a selected large exit aperture concentric with said input aperture, and C. locating said reflective means of said first scanning device at a conjugate plane of said output aperture.

24. A method according to claim 22 comprising the further step of locating means for detecting said output beam at a conjugate plane of the fundus being scanned with said input beam.

25. A scanning opthalmoscope for providing a two-dimensional output representation of reflection charactertistics of the eye fundus, said apparatus comprising, a laser source for generating a laser beam of defined cross section area which is small compared to an area of the fundus which is to be scanned, an optical system for directing said laser beam through the pupil of the eye onto said fundus area, said optical system including, a first scanning element comprising a rotating reflector and driving means for rotating said rotating reflector to scan said laser beam along a first coordinate across an area of said fundus, a turning mirror having a reflecting surface just large enough to encompass the defined cross sectional area of said laser beam, said turning mirror being positioned to intercept said laser beam and redirect it onto said first scanning element, a first focusing mirror for directing said laser beam from said first scanning element through the eye pupil onto the fundus area, an exit aperture for reflected light from said scanned fundus area, said exit aperture being large compared to the cross sectional dimensions of said laser beam, said first focusing mirror being positioned to produce at the surface of said rotating reflector a conjugate image of said eye pupil, the cross sectional area of said eye pupil image being allowed to be large compared to the dimension of the facets of said rotating reflector along the coordinate of scan, a detector means positioned optically beyond said turning mirror to receive reflected light from said first focusing mirror from said rotating reflector which passes back along the path toward said turning mirror, said turning mirror providing a stop for only the central portion of said reflected beam, said detector means generating a signal varying in time with the amount of light reflected from said rotating reflector onto said detector means, and display means for providing said two-dimensional output representation of said eye fundus in response to said detector signal.

26. An ophthalmoscope apparatus in accordance with claim 25 wherein said first scanning element is a multi-faceted polygon.

27. An ophthalmoscope apparatus in accordance with claim 25 wherein said optical system further includes, a second scanning element arranged in optical alignment between said first scanning element and the eye fundus to be scanned for moving said scanning laser beam in a direction normal to said first coordinate to effect a two-dimensional scan of said retinal area, and a second focusing mirror positioned between said first and second scanning elements for directing the laser beam reflected from the facet of said polygonal reflector onto the surface of said second scanning means.

28. An ophthalmoscope apparatus in accordance with claim 27 wherein said first scanning element is a multi-faceted polygon.

29. An ophthalmoscope apparatus in accordance with claim 25 wherein said detector means is an avalanche diode.

30. Apparatus in accordance with claim 25 wherein said detector is placed at the retinal conjugate plane.

* * * * *